United States Patent [19]

Lamberti et al.

[11] 4,167,524

[45] Sep. 11, 1979

[54] CARBOXYMETHYLOXYSUCCINIC ANHYDRIDES, HALIDES AND DERIVATIVES THEREOF

[75] Inventors: Vincent Lamberti, Upper Saddle River; Gutierraz Eddie N., Fort Lee, both of N.J.

[73] Assignee: Lever Brothers Company, New York, N.Y.

[21] Appl. No.: 893,232

[22] Filed: Apr. 4, 1978

Related U.S. Application Data

[62] Division of Ser. No. 797,226, May 16, 1977, Pat. No. 4,093,634.

[51] Int. Cl.[2] .............................................. C07C 55/22
[52] U.S. Cl. ................................................. 260/544 Y
[58] Field of Search ..................................... 260/544 Y

[56] References Cited

U.S. PATENT DOCUMENTS 3,914,297  10/1975  Lamberti et al. ................ 260/535 P

OTHER PUBLICATIONS

Morrison & Boyd, "Organic Chemistry," 3rd Ed., pp. 658–664, (1973).

*Primary Examiner*—Gerald A. Schwartz
*Attorney, Agent, or Firm*—James J. Farrell; Melvin H. Kurtz; Ira J. Schultz

[57] ABSTRACT

Carboxymethyloxysuccinic anhydrides and/or halides, their reaction products with active hydrogen compounds and methods for preparing the anhydrides, the halides and the reaction products are disclosed. The reaction products are variously useful in the fields of food flavorings, detergent builders, surfactants, lubricants, coatings, sizing agents and gasoline additives.

2 Claims, No Drawings

CARBOXYMETHYLOXYSUCCINIC ANHYDRIDES, HALIDES AND DERIVATIVES THEREOF

This application is a divisional of Ser. No. 797,226, filed May 16, 1977, now U.S. Pat. No. 4,093,634.

BACKGROUND OF THE INVENTION

Carboxymethyloxysuccinic acid, hereinafter referred to as CMOSA, is a known, highly biodegradable ether tricarboxylic acid which is conveniently prepared from maleic anhydride and glycolic acid as described in U.S. Pat. No. 3,914,297 incorporated herein by reference. CMOSA is unique compared to the most similar, structurally analogous ether polycarboxylic acid, namely, oxydiacetic acid. Thus, CMOSA is a relatively safe substance having known utility as a food acidulant and flavoring material (see U.S. Pat. No. 4,015,023) whereas oxydiacetic acid is a known toxic substance. Accordingly, introduction of a carboxymethyloxysuccinic acid residue into an organic molecule to obtain useful polyfunctionality while at the same time not impairing the biodegradability or safety characteristics of the molecule has become a desirable objective.

It is therefore an object of this invention to provide methods for preparing the anhydrides and acid halides of carboxymethyloxysuccinic acid.

It is also an object of this invention to provide useful novel derivatives of the anhydrides and acid halides of carboxymethyloxysuccinic acid.

These and other objects will become apparent as the description proceeds.

The attainment of the above objects is made possible by the conversion of CMOSA into novel anhydrides and/or acid halides. The anhydride and acid halide products are reacted with selected active hydrogen compounds such as water, hydrogen sulfide, ammonia, amines, alcohols, polyols, carbohydrates, amino acids and the like to produce a variety of useful derivatives of carboxymethyloxysuccinic acid.

DETAILED DESCRIPTION OF THE INVENTION

I. Preparation of anhydrides and acid halides

Carboxymethyloxysuccinic acid is converted into anhydride species by reaction with either: (1) excess acetyl chloride either alone or in the presence of pyridine or (2) excess acetic anhydride. These methods afford mainly a mixture of anhydride species containing five- and six-membered rings as well as polymeric species. This mixture may be represented by the general structural formulae as follows:

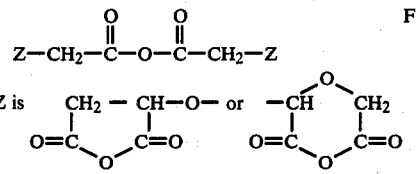

Formula I

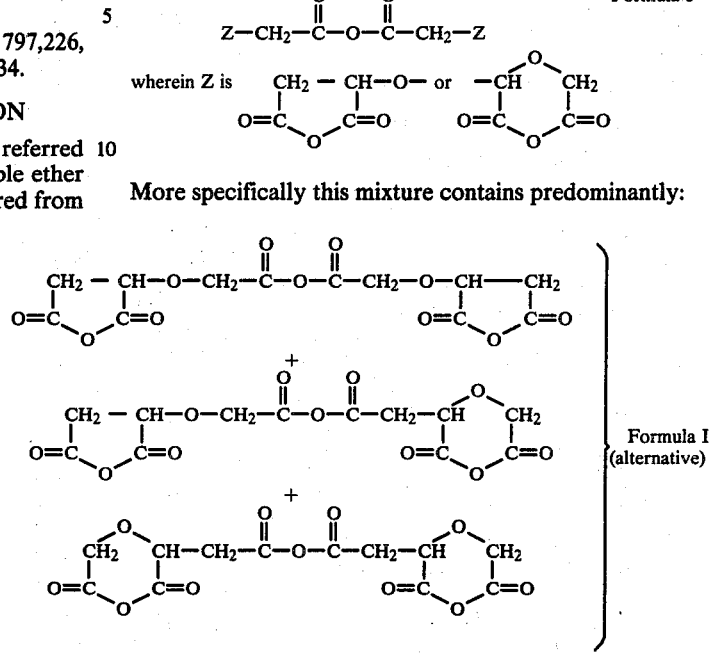

More specifically this mixture contains predominantly:

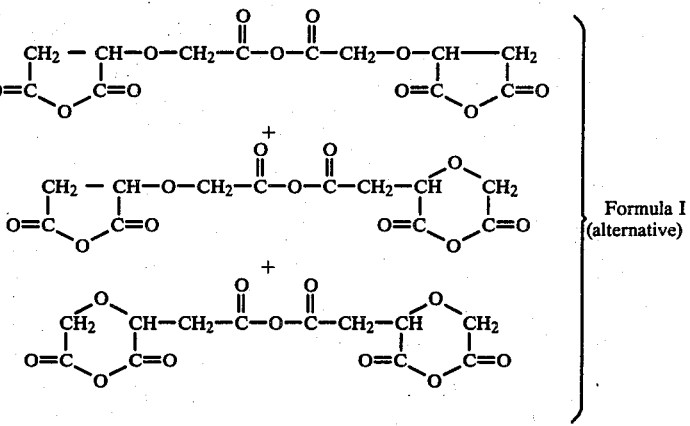

Formula I (alternative)

The above mixture of CMOS anhydride species will be subsequently referred to as Formula I.

A predominantly mono anhydride species of carboxymethyloxysuccinic acid can be prepared by dehydration of CMOSA by the following methods: (1) heating CMOSA in a vacuum, (2) subjecting CMOSA to azeotropic distillation with a suitable solvent such as 1,1,2,3-tetrachloroethane or xylene and (3) reaction of one mole of acetyl chloride or thionyl chloride per mole of carboxymethyloxysuccinic acid in a suitable solvent such as dioxane, ether or tetrahydrofuran. The structure of this species is predominantly the five-membered ring species,

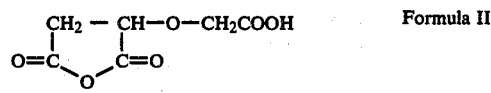

Formula II and will be referred to henceforth as Formula II.

In many instances the Formula II anhydride is preferred for preparing derivatives since there is only one anhydride ring per molecule. In this way reaction with an active hydrogen compound introduces only one mole of the active hydrogen compound per mole of the Formula II anhydride.

A mixed anhydride chloride species, hereinafter designated as Formula III, is obtainable by reaction of at least two moles of a thionyl halide per mole of carboxymethyloxysuccinic acid. The product of this reaction contains predominantly the following chemical species:

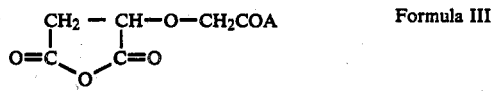

Formula III wherein A is Cl, Br or I and preferably Cl.

By reaction with excess thionyl halides or phosphorus tri- or penta-halides in the presence of zinc halides, the compounds of Formula I, II or III can be converted into carboxymethyloxysuccinic trihalides of the formula:

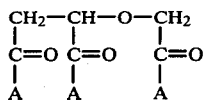
Formula IV wherein A is Cl, Br or I and preferably Cl.

The reactions utilized in the above preparations of the species of Formulas I and IV are applications of known methods or combinations of known methods for preparing organic acid anhydrides and acid chlorides. Examples of such methods are those described in the text entitled "Synthetic Organic Chemistry" by R. B. Wagner and H. D. Zook, John Wiley & Sons, 1953, pp. 546–549 (especially section numbers 335, 337 and 338) and pp. 558–559 (especially section numbers 341 and 343) and the references cited therein (all of which are incorporated herein by reference). Specific illustrative preparations of the anhydride and/or acid halide species of carboxymethyloxysuccinic acid will be found in the Examples of this specification.

The species of Formulas I, II, III and IV may also be reacted with various active hydrogen compounds to produce useful derivatives. The species of Formulas III and IV are chemically more reactive than those of Formulas I and II. Also, the Formula III species produces the same derivatives as those of Formula I. Accordingly, in the description that follows it will be understood that whenever reactions of Formula I are described, the same reactions apply to Formula III. Formula IV species is unique compared to the other species in that reactions with active hydrogen compounds leads to trisubstitution (e.g. reaction of Formula IV species with methanol giving rise to trimethyl carboxymethyloxysuccinate).

A non-limiting list of active hydrogen compounds which are useful for reaction with species of Formulas I, II, III and IV is as follows: water; hydrogen sulfide; hydroxyl compounds such as straight or branched aliphatic alcohols containing one to twenty-four carbon atoms as exemplified by methanol, ethanol, isopropanol, butanol, octanol, dodecanol and the like; alicyclic alcohols such as cyclopentanol and cyclohexanol; phenol and substituted phenols such as cresol, anisole, the halo phenols and the like; polyols such as ethylene glycol, propylene glycol, 1,2-dihydroxybutane, 1,3-dihydroxybutane, 1,4-dihydroxybutane, glycerol, pentaerythritol, sorbitol, mannitol, inositol and the like; carbohydrates such as glucose, sucrose, starch, cellulose, dextrins and the like; ammonia and amines such as the straight or branched alkylamines containing one to about twenty two carbon atoms as exemplified by methyl amine, ethyl amine, butyl amine, dodecyl amine and the like; alkylolamines such as monoethanolamine, diethanolamine, isopropanol amine, 2-hydroxybutyl amine and the like; hydrazine and alkane diamines wherein the alkane group contains 1 to 12 carbons such as ethylene diamine, propane-1,3-diamine, butane-1,4-diamine, hexane-1,6-diamine and the like; amino acids such as glycine, sarcosine, α- and β-alanine, glutamic acid and the like and esters thereof; the thiol analogs of the foregoing such as the straight or branched alkyl mercaptans containing 1 to 12 carbon atoms as exemplified by methyl mercaptan, butyl mercaptan, dodecyl mercaptan and the like; 2-mercaptoethanol, 1,2-dimercaptoethane, α- and β-thioglycerol thiophenol and the like.

More specific and preferred examples are as follows.

A. Reaction of the species of Formulas I, II, III or IV with water yields the starting CMOSA and thus represents a method of purifying crude preparations of CMOSA especially when the anhydride and/or acid chloride has been subjected to a purification step prior to reaction with water. Thus, the species of Formula I may be precipitated out of an organic solvent such as methylene chloride/acetone at about −70° C. to yield a purified product which is then heated with excess water. Purified carboxymethyloxysuccinic acid may then be separated from the resulting solution by known methods such as evaporation in vacuo at temperatures below about 100° C.

B. Reaction of the species of Formulas I, II, III and IV with hydrogen sulfide and/or an alkali metal hydrosulfide or a tertiary amine hydrosulfide produces thiolcarboxymethyloxysuccinic acids of the following general structure (Formula V)

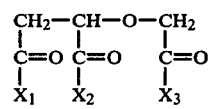
Formula V wherein $X_1$, $X_2$ and $X_3$ is OH or SH and at least one of $X_1$, $X_2$ and $X_3$ is SH. These compounds are useful as foodstuff flavoring compounds and as metal ion sequestrants. In the form of the alkali metal, ammonium and alkylolammonium salts, the compounds or the hydrated forms thereof, are useful as both metal ion sequestrants and detergents builders.

It will be understood that thiolcarboxymethyloxysuccinic acids prepared from the species of Formulas I and III will be a mixture of thiolcarboxymethyloxysuccinic acids containing predominantly the following structures (Formula VI)

$$\left.\begin{array}{c} \text{CH}_2-\text{CH}-\text{O}-\text{CH}_2 \\ | \quad | \quad\quad | \\ \text{C}=\text{O} \;\; \text{C}=\text{O} \quad \text{C}=\text{O} \\ | \quad | \quad\quad | \\ \text{SH} \quad \text{OH} \quad\;\; \text{OH} \\ + \\ \text{CH}_2-\text{CH}-\text{O}-\text{CH}_2 \\ | \quad | \quad\quad | \\ \text{C}=\text{O} \;\; \text{C}=\text{O} \quad \text{C}=\text{O} \\ | \quad | \quad\quad | \\ \text{SH} \quad \text{OH} \quad\;\; \text{SH} \\ + \\ \text{CH}_2-\text{CH}-\text{O}-\text{CH}_2 \\ | \quad | \quad\quad | \\ \text{C}=\text{O} \;\; \text{C}=\text{O} \quad \text{C}=\text{O} \\ | \quad | \quad\quad | \\ \text{OH} \quad \text{SH} \quad\;\; \text{OH} \\ + \\ \text{CH}_2-\text{CH}-\text{O}-\text{CH}_2 \\ | \quad | \quad\quad | \\ \text{C}=\text{O} \;\; \text{C}=\text{O} \quad \text{C}=\text{O} \\ | \quad | \quad\quad | \\ \text{OH} \quad \text{SH} \quad\;\; \text{OH} \end{array}\right\} \text{Formula VI}$$

Thiolcarboxymethyloxysuccinic acids prepared from the species of Formula II will contain predominantly the following structures (Formula VII):

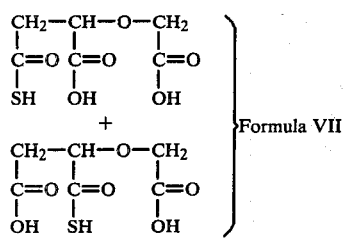

Formula VII

Further, thiolcarboxymethyloxysuccinic acid prepared from the species of Formula IV will be the single trithiol species (Formula VIII):

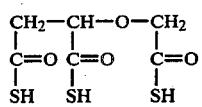

Formula VIII

The various thiolcarboxymethyloxysuccinic acids described above (i.e., Formulas VI, VII and VIII) are obtainable by applying the known methods for converting acetic anhydride or mixed anhydrides into thiol acids. Thus, the methods of U.S. Pat. No. 2,412,036 and of Cronyn, et al, J.A.C.S. 74 4726 (1956), both of which are incorporated herein by reference are applicable. In applying the Cronyn, et al procedure, dioxane may be substituted for methylene chloride in order to increase the solubility of the CMOSA anhydride or chloride species in the reaction medium. The crude thiolcarboxymethyloxysuccinic acid reaction products obtained by these methods are purified by first evaporating any organic solvent present, dissolving the remaining residue in water and passing the resulting aqueous solution through a column of cation exchange resin. Evaporation of the eluate in vacuo leaves the purified thiolcarboxymethyloxysuccinic acid(s) as a residue or, if desired, the evaporation can be interrupted to provide a concentrated aqueous solution (e.g. containing ca. 40–50% thiolcarboxymethyloxysuccinic acid(s)).

The following species (Formula IX) of thiolcarboxymethyloxysuccinic acid,

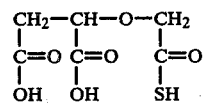

Formula IX is not present to any significant extent in any of the above preparations of thiolcarboxymethyloxysuccinic acids (i.e. Formulas VI, VII and VIII). It is entirely possible, however, that this species, (i.e. Formula IX) may be made from thiolglycolic acid

(i.e. HOCH$_2$C—SH)

and maleic acid using the teachings of U.S. Pat. No. 3,914,297 which describe the preparation of CMOSA.

C. Reaction of the species of Formulas I, II or III with ammonia or a primary or secondary alkyl amine produces amido ether polycarboxylate salts or mixtures of their salts having the following general formula:

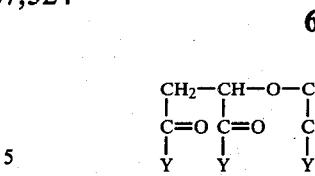

(Formula X)

wherein Y is independently NH$_2$, NRR' or OM and at least one Y is always OM; wherein R is an alkyl group containing 6 to 22 carbon atoms or an alkylol group R$_2$OH, wherein R$_2$ contains two to four carbon atoms; wherein R' is either H or R as defined above and wherein M is ammonium or a RR'+NH$_2$ cation.

The reaction is readily carried out using an aqueous solution of the amine in those cases where the amines are soluble in water and at temperatures ranging from room temperature to about 50° C. In those cases where the amines are insoluble in water or are liquid at or above room temperature, an excess of the amine is utilized as the reaction solvent or an inert solvent such as diethyl ether, dibutyl ether and tetrahydrofuran is utilized. The Formulas I, II or III species are added to the amine or solution of amine. Preferably, about six moles of amine are utilized per mole of Formula I species; three moles of amine, per mole of Formula II species and four moles of amine, per mole of Formula III species. Reaction conditions from room temperature to the boiling point of the solvent utilized or to about 100° C. are sufficient for the reaction. The reaction mixture is initially cooled during the slow addition of the species of Formulas I, II or III because of the exothermic nature of the reaction.

When Formula I or III species are utilized, the product will be a mixture of mono- and di-substituted amide derivatives of carboxymethyloxysuccinic acid (i.e. one or two of the Y substituents of Formula X is NRR').

When the Formula II species is utilized, the product will contain only one amide group per molecule (i.e. one Y substituent in Formula X is NRR').

In all cases the reaction products may be treated with an alkali metal hydroxide or carbonate to release the amine combined with carboxyl groups or hydrogen halide as salts, thereby producing compounds containing both amido functions and alkali metal carboxylate functions. The products are then purified by trituration with a suitable solvent such as ether, acetone or alcohol and filtration, thereby removing the liberated amine. Addition purification may be readily accomplished by acidification of the product with aqueous mineral acid and filtration to recover the acid forms of the desired products where M in Formula X is H. The acid forms are then washed with water and neutralized with an aqueous alkali metal hydroxide, ammonia or with a substituted ammonium compound such as monoethanolamine, diethanolamine, triethanolamine, isopropanolamine, diisopropanolamine, triisopropanolamine or morpholine to produce useful surface active agents having the following general structure:

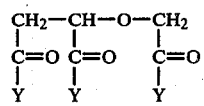

Formula XA wherein Y is independently NH$_2$, —NRR' or OM$_1$, and at least one Y is always OM$_1$; wherein R is an alkyl group containing 6 to 22 carbon atoms or an alkyl group R$_2$OH wherein R$_2$ contains two to four carbon atoms;

and wherein R' is H or R as defined above and wherein $M_1$ is H, an alkali metal, ammonium or a substituted ammonium cation selected from the group consisting of monoethanolammonium, diethanolammonium, triethanolammonium, isopropanolammonium, diisopropanolammonium, triisopropanolammonium and morpholinium cations.

For example, the following predominant amido ether carboxylate products, Formula XI, are obtained by starting with the Formula III species in the above reaction and purification sequence.

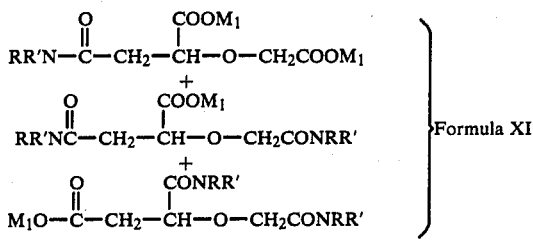
Formula XI wherein $M_1$, R and R' are as defined above.

When Formula I species is utilized in the above reaction and purification sequence, the product is a complex mixture containing not only the species of Formula XI but additional species such as

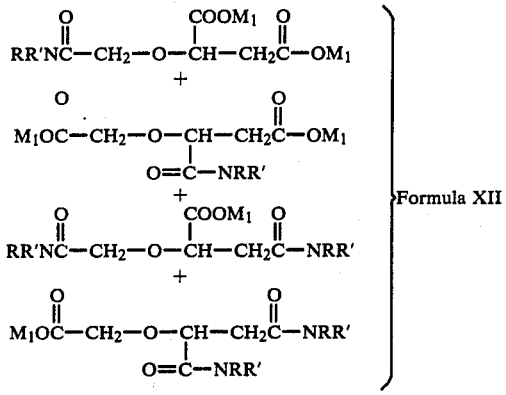
Formula XII wherein $M_1$, R and R' have the same meanings as defined above.

In the case where Formula II species is utilized in the above reaction and purification sequence, the product is predominantly a mixture of the first two structures shown in Formula XI above.

The preferred amido ether carboxylate compounds for detergent properties are those in which R is selected from the group $C_{10}$ to about $C_{22}$ alkyl chains (primary or secondary) and R' is H or an alkyl group containing one to about 6 carbon atoms and $M_1$ is a sodium or potassium cation. The preferred groups for wetting action are those compounds in which R contains $C_5$ to about $C_9$ alkyl chains (primary or secondary), R' is H or equal to R and $M_1$ is a sodium or potassium cation.

The aforesaid amido ether carboxylates are useful not only in detergent compositions for washing fabrics and hard surfaces but also in personal cleaning compositions such as toilet bars, shampoos, hair rinses, skin cleansing compositions and dentifrice products.

When the formula IV species is reacted with ammonia or with alkyl amines using the reaction conditions described above for reactions of Formulas I, II and III species with the same active hydrogen compounds and using at least six moles of ammonia or amine per mole of Formula IV species, there is obtained the triamide or trisubstituted amides of carboxymethyloxysuccinic acid:

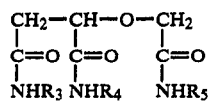
Formula XIII wherein $R_3$, $R_4$ and $R_5$, which may be the same or different are selected from the group consisting of hydrogen, a straight or branched chain hydrocarbon radical having from 1 to 18 carbon atoms and an alkylol group $R_6OH$ wherein $R_6$ contains two to four carbon atoms. Such compounds have utility in the fields of lubricants and textile sizing as disclosed in U.S. Pat. No. 3,959,373 assigned to the instant assignee.

The compounds of Formula XIII are readily isolated and purified using the purification technique described above for isolating the amido ether carboxylic acid compounds (Formula X, M=H) free of ammonia or amine reactant and finally purifying the product according to methods described in U.S. Pat. No. 3,959,373 (incorporated herein by reference).

D. In an additional embodiment of the invention, the Formula I, II and III species are reacted with hydroxyl containing compounds to produce partial esters or carboxymethyloxysuccinic acid:

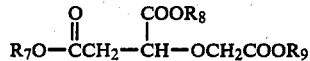
Formula XIV wherein $R_7$, $R_8$ and $R_9$ represent hydrogen or hydrocarbyl radicals containing 1 to 24 carbon atoms and at least one of the $R_7$, $R_8$ and $R_9$ groups is hydrogen. Some non-limiting representative examples of hydrocarbyl radicals are alkyl, cycloalkyl, alkenyl, aralkyl, alkaryl and aryl groups.

A preferred group of the hydroxyl containing compounds which may be utilized are the alkanols containing 1 to 20 carbon atoms. The resulting partial esters of carboxymethyloxysuccinic acid (Formula XIV) are useful as additives in non-leaded gasoline as described in U.S. Pat. No. 3,926,580 which is incorporated herein by reference.

The partial esters may be completely esterified by conventional techniques to produce the tri-hydrocarbyl esters of carboxymethyloxysuccinic acid. These materials have known utility as detergent solvents and plasticizers (U.S. Pat. No. 3,943,165).

When Formula IV species are reacted with the alkanols containing 1 to 20 carbon atoms the tri-hydrocarbyl esters of carboxymethyloxysuccinic acid are obtainable directly. These derivatives are also useful in non-leaded gasoline as described in U.S. Pat. No. 3,926,580.

Other hydroxy compounds which may be reacted with Formula I, II, III and IV species to produce useful derivatives are: polyols such as ethylene glycol, propylene glycol, glycerol, pentaerythritol and sorbitol; carbohydrates such as glucose, sucrose, starch, cellulose and oligosaccharides such as dextrins and hydrolyzed forms of starch and cellulose. The reaction products with the polymeric carbohydrates (e.g. starch) are useful for producing edible films, coatings, adhesives and detergent builders.

E. Similarly, Formula I, III and IV species may be reacted with polyamines such as ethylene diamine and propylene diamine to produce polymeric materials having useful properties for use in coatings, adhesives and humectant systems.

Having thus described the invention and its several and preferred embodiments, the following are detailed examples of the invention.

In the Examples below the structures of the products were confirmed by NMR (Varian T60 instrument) and/or infrared (Beckman IR-5A). All parts and percentages are by weight unless otherwise specified.

EXAMPLE 1

Preparation of Mixed Carboxymethyloxysuccinic Anhydrides—Formula I

One hundred grams (0.29 mole) of trisodium carboxymethyloxysuccinate pentahydrate is placed in a flask and acidified with 90 mls of 37% hydrochloric acid while stirring and cooling the mixture in an ice bath. The reaction mixture is then evaporated to dryness in vacuo. The evaporation residue is then taken up in about 150 ml acetone and filtered to remove sodium chloride. The acetone filtrate is next evaporated to dryness to give essentially pure carboxymethyloxysuccinic acid as a residue.

The carboxymethyloxysuccinic acid from above is mixed with 100 mls of acetyl chloride in a reaction flask equipped with a condenser. The resulting mixture refluxed until all of the acid is dissolved and the evolution of hydrogen chloride has essentially ceased. The reaction mixture is then evaporated in vacuo to form a syrupy residue. The syrup residue is mixed with about 100 mls of methylene chloride and the resulting solution heated while acetone is gradually added until a complete solution occurs. The resulting solution is then cooled to $-70°$ C. (dry ice/acetone bath) and the solid which crystallizes out is immediately filtered by suction and placed in a vacuum dessicator. The solid, which liquifies at room temperature, is shown by infrared analysis to consist of a mixture of five-membered (5.36 $\mu$) and six-membered anhydride (5.8 $\mu$) species together with linear anhydride polymers.

EXAMPLE 2

Preparation of Carboxymethyloxysuccinic Mono Anhydride—Formula II

A. Ten grams of carboxymethyloxysuccinic acid (95.5% pure; 3% moisture), 0.2 g of p-toluenesulfonic acid monohydrate and 300 mls of xylene are placed in a 500 ml flask equipped with a condenser and Dean Stark apparatus. The mixture is then refluxed for three hours during which time 1 ml water separates in the water separator. The xylene layer is decanted and the remaining syrupy residue is taken up in 150 ml of acetone. The acetone is evaporated to a syrupy residue which is then placed in a vacuum oven at 90° C. to remove residual traces of solvents. The product, 8 g, is shown by infrared analysis to consist of a mixture containing predominantly five-membered anhydride species containing free carboxyl groups.

B. To 10 g (0.05 mole) of 95.5% CMOSA dissolved in 17 g of dioxane is added 8 g (0.067 mole) of thionyl chloride. The solution is then refluxed for forty minutes. The solution is then evaporated in vacuo to remove solvent and any excess thionyl chloride. A liquid residue of 9.4 g containing predominantly the desired product of Formula II was obtained. Infrared analysis confirmed the presence of a five-membered anhydride moiety (5.35 $\mu$) and the characteristic band for COOH stretching (2.8–4.4 $\mu$).

EXAMPLE 3

Preparation of Monomethyl Dihydrogen Carboxymethyloxysuccinate

Two grams of Formula II species prepared as described in Example 2 is dissolved in 10 ml of methanol by heating to reflux. The methanolic solution is then evaporated in vacuo to give a liquid residue of a mixture of monomethyl esters of carboxymethyloxysuccinic acid. NMR analysis shows the presence of three distinct types of methyl ester groups (3.74$\delta$, 3.80$\delta$ and 3.81$\delta$) corresponding to the three different types of carboxyl groups possible in carboxymethyloxysuccinic acid.

The presence of the three types of ester groups instead of the expected two is believed to be due to a randomization of the methyl groups among all the possible carboxyl groups during the reaction and work up.

EXAMPLE 4

Preparation of Chlorocarbonylmethyloxysuccinic anhydride - (Formula III, A=Cl)

Carboxymethyloxysuccinic acid, 18.8 g (95.5% purity; 0.094 mole) is mixed with 48 g (0.41 mole) thionyl chloride and 100 mls of chloroform. The resulting mixture is refluxed for three hours thereby producing a light yellow reaction solution. The reaction solution is evaporated in vacuo to give 17.2 g of the desired compound. NMR and infrared analysis of the compound are consistent with predominantly a five-membered anhydride ring and acid chloride function:

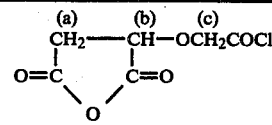

NMR (CDCl$_3$):

CH$_2$(a) ABX multiplet at 2.80–3.80$\delta$
CH(b) ABX multiplet at 4.60–5.00$\delta$
CH$_2$(c) singlet at 4.89$\delta$ Infrared:

5-membered anhydride carbonyl, 5.35$\delta$
acid chloride (COCl) carbonyl, 5.56$\delta$
—OH-stretching band for —COOH is absent

EXAMPLE 5

Preparation of Dimethyl Hydrogen Carboxymethyloxysuccinates

One gram of the mixed anhydride acid chloride of carboxymethyloxysuccinic acid prepared as described in Example 4 is dissolved in 10 mls of methanol. The solution is then evaporated and the residue warmed gently in vacuo to remove the last traces of methanol. NMR (DCl$_3$) analysis of the residue is consistent with a mixture of the following dimethyl esters of carboxymethyloxysuccinic acid:

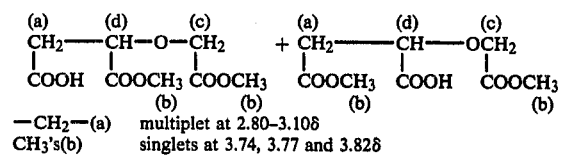

—CH$_2$—(a) multiplet at 2.80–3.10$\delta$
CH$_3$'s(b) singlets at 3.74, 3.77 and 3.82$\delta$ -continued —CH₂—(c) and
—CH—(d) mixed singlet and multiplet at 4.34–4.64δ

EXAMPLE 6

Preparation of Carboxymethyloxysuccinic Trichloride (Formula IV, A=Cl)

Thionyl chloride, 23 g (0.17 mole), is added to a mixture of 5 g of 95.5% (0.025 mole) carboxymethyloxysuccinic acid and 0.5 g of anhydrous zinc chloride. The resulting mixture is stirred at 25° C. until the CMOSA dissolves (about 2 hours). The clear reaction solution is decanted into a clear flask and the excess thionyl chloride is distilled off in vacuo (water pump). The residue, 4 g, is identified as the desired product by NMR (CDCl₃):

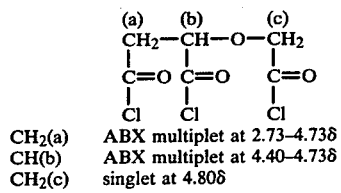

CH₂(a) ABX multiplet at 2.73–4.73δ
CH(b) ABX multiplet at 4.40–4.73δ
CH₂(c) singlet at 4.80δ

EXAMPLE 7

Preparation of Trimethyl Carboxymethyloxysuccinate

One-half gram of carboxymethyloxysuccinic trichloride prepared as described in Example 6 is dissolved in 5 ml methanol, heated for a few minutes and then the excess methanol is distilled off in vacuo (water pump).

The NMR (CDCl₃) spectrum of the residue is identical to that of authentic trimethyl carboxymethyloxysuccinate prepared by esterification of CMOSA with methanol according to the method of U.S. Pat. No. 3,943,165.

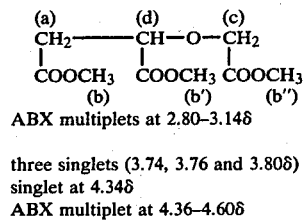

CH₂(a) ABX multiplets at 2.80–3.14δ
CH₃(b,b' and b") three singlets (3.74, 3.76 and 3.80δ)
CH₂(c) singlet at 4.34δ
CH(d) ABX multiplet at 4.36–4.60δ

Modifications will occur to those skilled in the art in view of the foregoing description and such modifications are to be included within the purview of the invention.

What is claimed is:

1. Carboxymethyloxysuccinic trihalides of the formula:

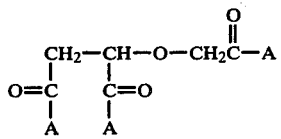

wherein A is Cl, Br or I.

2. The compound of claim 1 wherein A is Cl.

* * * * *

UNITED STATES PATENT AND TRADEMARK OFFICE
CERTIFICATE OF CORRECTION

PATENT NO. : 4,167,524
DATED : September 11, 1979
INVENTOR(S) : Vincent Lamberti and Eddie N. Gutierrez It is certified that error appears in the above-identified patent and that said Letters Patent are hereby corrected as shown below:

<u>Title Page</u>: Change "Gutierraz" to --Gutierrez--.

Column 7, lines 31-33: Change

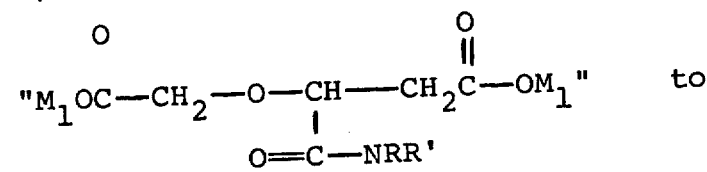

to

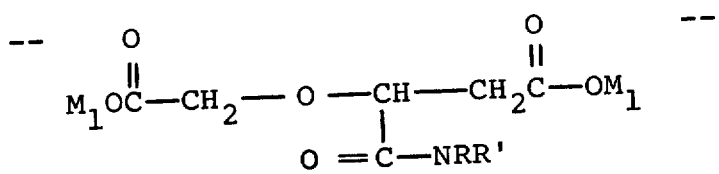

Column 10, line 59: change "NMR ($DCl_3$) to -- NMR ($CDCl_3$) --.

Signed and Sealed this

Twenty-second Day of January 1980

[SEAL]

Attest:

SIDNEY A. DIAMOND

Attesting Officer

Commissioner of Patents and Trademarks